(12) United States Patent
Noda

(10) Patent No.: US 10,398,311 B2
(45) Date of Patent: Sep. 3, 2019

(54) FUNDUS IMAGE FORMING DEVICE

(71) Applicant: NIKON CORPORATION, Minato-ku, Tokyo (JP)

(72) Inventor: Tomoya Noda, Saitama (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 15/630,324

(22) Filed: Jun. 22, 2017

(65) Prior Publication Data

US 2017/0347881 A1  Dec. 7, 2017

Related U.S. Application Data

(63) Continuation of application No. PCT/JP2014/084630, filed on Dec. 26, 2014.

(51) Int. Cl.
*A61B 3/10* (2006.01)
*A61B 3/12* (2006.01)
(Continued)

(52) U.S. Cl.
CPC ............... *A61B 3/12* (2013.01); *A61B 3/10* (2013.01); *A61B 3/1025* (2013.01); *A61B 3/14* (2013.01); *G02B 17/0621* (2013.01)

(58) Field of Classification Search
CPC ........... A61B 3/12; A61B 3/10; A61B 3/1025; A61B 3/14; G02B 17/06
(Continued)

(56) References Cited

U.S. PATENT DOCUMENTS 5,815,242 A     9/1998   Anderson et al.
6,879,747 B2 *  4/2005   Ikegame .............. G01R 5/10
                                                     359/196.1
(Continued)

FOREIGN PATENT DOCUMENTS

JP     2009-543585 A    12/2009
JP     2010-508932 A     3/2010
(Continued)

OTHER PUBLICATIONS

International Preliminary Report on Patentability and Written Opinion of the International Searching Authority issued in International application No. PCT/JP2014/084630 dated Jun. 27, 2017.
(Continued)

*Primary Examiner* — Collin X Beatty
(74) *Attorney, Agent, or Firm* — Foley & Lardner LLP

(57) ABSTRACT

A fundus imaging system comprises: a first reflection mirror that reflects a light beam passing through a first focus of the first reflection mirror to pass through a second focus; a two-dimensional scanning unit that is disposed at a position of the first focus and reflects a light beam incident on the two-dimensional scanning unit so as to scan the retina with the light beam in two-dimensional directions; and a second reflection mirror that reflects a light beam passing through a third focus so as to cause the light beam to pass through a fourth focus, the second reflection mirror being disposed so that a position of the third focus coincides with a position of the second focus, wherein a position of the pupil of the subject is disposed so as to coincide with a position of the fourth focus.

20 Claims, 5 Drawing Sheets

(51) Int. Cl.
*A61B 3/14* (2006.01)
*G02B 17/06* (2006.01)

(58) Field of Classification Search
USPC .................................................. 351/206
See application file for complete search history.

(56) References Cited

U.S. PATENT DOCUMENTS

| | | | |
|---|---|---|---|
| 9,271,644 B2 * | 3/2016 | Azegrouz | A61B 3/1025 |
| 9,566,001 B2 * | 2/2017 | Katashiba | A61B 3/12 |
| 9,949,638 B2 * | 4/2018 | Creasey | A61B 3/0008 |
| 2010/0141895 A1 | 6/2010 | Cairns et al. | |
| 2010/0150415 A1 | 6/2010 | Atkinson et al. | |
| 2012/0133888 A1 | 5/2012 | Gray et al. | |
| 2012/0188614 A1 | 7/2012 | Azegrouz | |
| 2013/0093996 A1 | 4/2013 | Thomson et al. | |
| 2013/0135583 A1 | 5/2013 | Gray et al. | |
| 2013/0335703 A1 | 12/2013 | Creasey et al. | |
| 2014/0327882 A1 | 11/2014 | Muyo et al. | |

FOREIGN PATENT DOCUMENTS

| | | |
|---|---|---|
| JP | 2013-532039 A | 8/2013 |
| JP | 2014-502552 A | 2/2014 |
| WO | WO-2008/056110 A2 | 5/2008 |
| WO | WO-2012/000719 A1 | 1/2012 |
| WO | WO-2012/001382 A1 | 1/2012 |
| WO | WO 2012095620 A1 * 7/2012 ........... A61B 3/0008 |  |

OTHER PUBLICATIONS

International Search Report issued in International application No. PCT/JP2014/084630 dated Mar. 17, 2015.
Chinese Office Action dated Apr. 28, 2018 as issued in corresponding Application No. 2014800843443 with English Translation thereof.
Japanese Office Action dated Apr. 24, 2018 as issued in corresponding Application No. 2016-565831 with English Translation thereof.
Extended European Search Report dated Jul. 9, 2018 received in corresponding European Application No. 14909092.0.

* cited by examiner

– 1 –

FUNDUS IMAGE FORMING DEVICE

BACKGROUND

1. Technical Field

The present invention relates to a fundus imaging system.

2. Related Art

Examples of a fundus scanning device that scans a retina of a subject for imaging a fundus image of the subject include a device that: vertically scans the retina with a laser beam using a polygon mirror and concurrently causes the laser beam to be incident on a first elliptical mirror; horizontally scans the retina with a light beam reflected off the first elliptical mirror using an oscillating plane mirror and concurrently causes the light beam to be incident on a second elliptical mirror; and causes a light beam reflected off the second elliptical mirror to be incident on a pupil of the subject (see, for example, Patent Document 1).

Patent Document 1: Japanese Unexamined Patent Application Publication (Translation of PCT Application) No. 2009-543585

The above-described fundus scanning device, however, is disadvantageous in that the entire device is increased in size or maintenance of the device becomes difficult because an oscillating plane mirror as a mechanically driven optical system is disposed between a first elliptical mirror and a second elliptical mirror.

SUMMARY

According to a first aspect of the present invention, a fundus imaging system scanning a retina of a subject, including: a first reflection mirror that reflects a light beam incident on the first reflection mirror after passing through a first focus so as to cause the light beam to pass through a second focus; a two-dimensional scanning unit that is disposed at a position of the first focus of the first reflection mirror and reflects a light beam incident on the two-dimensional scanning unit so as to scan the retina with the light beam in two-dimensional directions; and a second reflection mirror that reflects a light beam incident on the second reflection mirror after passing through a third focus so as to cause the light beam to pass through a fourth focus, the second reflection mirror being disposed so that a position of the third focus coincides with a position of the second focus of the first reflection mirror, wherein a position of the pupil of the subject is disposed so as to coincide with a position of the fourth focus of the second reflection mirror.

The summary clause does not necessarily describe all necessary features of the embodiments of the present invention. The present invention may also be a sub-combination of the features described above.

DESCRIPTION OF EXEMPLARY EMBODIMENTS

Hereinafter, the present invention is described through the embodiments of the invention. However, the following embodiments do not limit the invention according to the scope of claim. Also, all the combinations of the features described in the embodiments are not necessarily essential to means provided by aspects of the invention.

Figure 1:
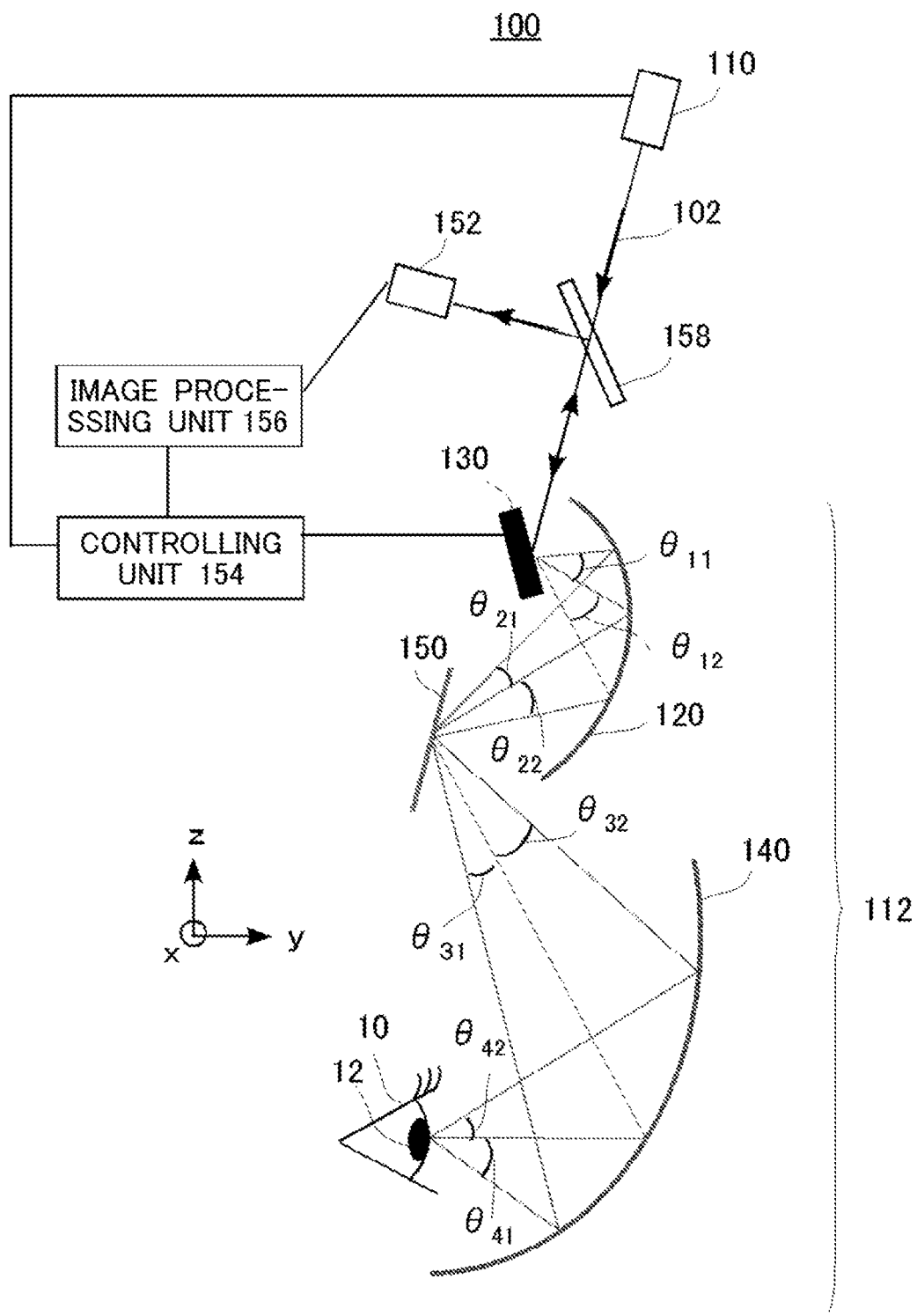
FIG. 1 is a schematic diagram of a fundus imaging system 100.

FIG. 1 is a schematic diagram of a fundus imaging system 100. The x, y and z directions are defined as shown in the figure. All of these are for description, and any of them may be in the vertical direction or in the horizontal direction.

The fundus imaging system 100 includes a light source 110, a half-silvered mirror 158, a scanning optical system 112, a detector 152, a controlling unit 154, and an image processing unit 156. The scanning optical system 112 has a two-dimensional scanning unit 130, a first reflection mirror 120, a plane reflection mirror 150, and a second reflection mirror 140.

The light source 110 emits a light beam 102 to illuminate an eye 10 of a subject. The wavelength of the light beam 102 may be selected according to a target of the inspection, and it is, for example, the infrared region wavelength, the visible light region wavelength, and the like. Although one light source 110 is shown in the example shown in FIG. 1, a plurality of light sources which emit light with different wavelengths may be used. When the plurality of light sources are used, light beams from respective light sources are placed on the same optical path by a beam combiner. Also, it is more preferable to use a laser light as the light beam because it has good linearity.

The half-silvered mirror 158 which functions as a beam splitter transmits and reflects the light beam incident on the half-silvered mirror 158 at a predesigned ratio. The half-silvered mirror 158 transmits the light beam 102 from the light source 110, and it reflects the light beam 102 returned from the eye 10 and leads the light beam to the detector 152. When the light beam 102 is multicolored, the half-silvered mirror 158 may be replaced with a plurality of dichroic mirrors corresponding to respective wavelengths, and a plurality of detectors which receive light beams reflected off respective dichroic mirrors may be provided.

Figure 2:
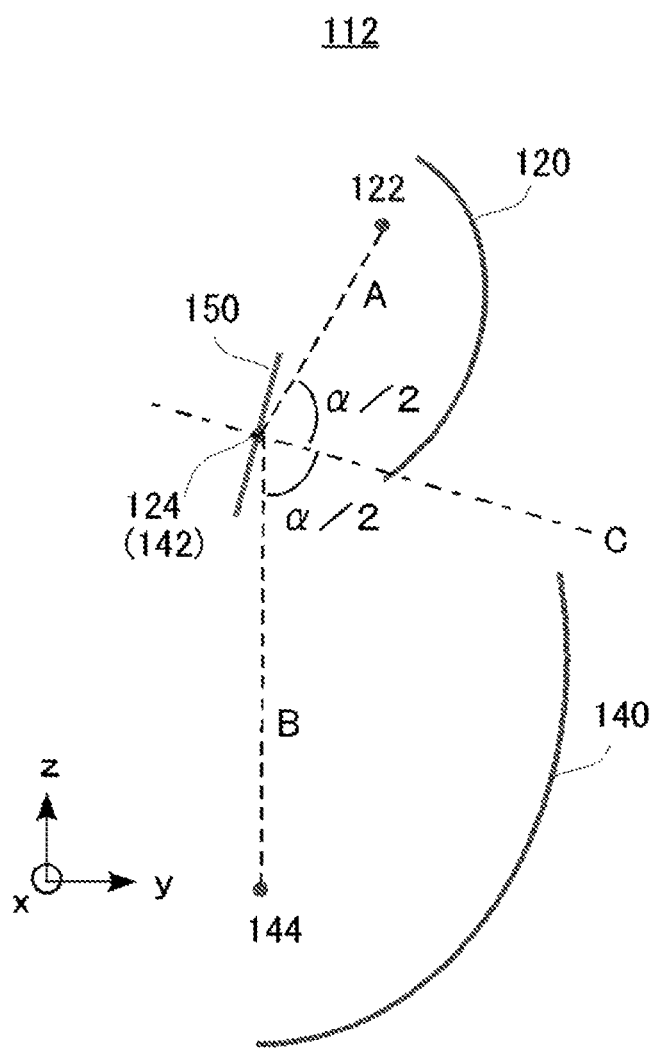
FIG. 2 is a schematic diagram illustrating an arrangement of a scanning optical system 112.

FIG. 2 is a schematic diagram illustrating an arrangement of the scanning optical system 112. Note that the two-dimensional scanning unit 130 is omitted for simplicity.

The first reflection mirror 120 has a first focus 122 and a second focus 124. The first reflection mirror 120 reflects a light beam 102 incident on the first reflection mirror 120 after passing through the first focus 122 so as to cause the light beam 102 to pass through the second focus 124. One example of the first reflection mirror 120 is an elliptical reflection mirror which has a reflection surface formed by a part of a rotary ellipsoid obtained by rotating an ellipse around a major axis including the first focus 122 and the second focus 124.

The second reflection mirror 140 has a third focus 142 and a fourth focus 144. The second reflection mirror 140 reflects a light beam 102 incident on the second reflection mirror 140 after passing through the third focus 142 so as to cause the light beam 102 to pass through the fourth focus 144. One example of the second reflection mirror 140 is an elliptical reflection mirror which has a reflection surface formed by a part of a rotary ellipsoid obtained by rotating an ellipse around a major axis including the third focus 142 and the fourth focus 144.

About the position of the third focus 142 of the second reflection mirror 140 and the position of the second focus 124 of the first reflection mirror 120, there may be cases where the respective positions are completely coincident as shown in FIG. 2, or, where they are the same in design, but are inevitably misaligned due to assembling error, etc.

The plane reflection mirror 150 is disposed at the position of the second focus 124 of the first reflection mirror 120. In an example shown in FIG. 2, the plane reflection mirror 150 is a plane mirror, the reflection surface thereof is disposed so as to pass through the second focus 124, the plane reflection mirror 150 may be fixed at least during scanning of the light beam 102, and the plane reflection mirror 150 may be moved for optical adjustment before or after scanning. Although it is preferable that the above-described positions of the plane reflection mirror 150 and the second focus 124, and furthermore, the previously described positions of the second focus 124 of the first reflection mirror 120 and the third focus 142 of the second reflection mirror 140 are ideally coincident respectively, coincidence of these positional relationships at a predetermined range is permitted. The range is a range that allows a scanning light beam to enter a pupil of an eye when the angle of the light beam is two-dimensionally scanned at an iris position of the subject's eye, and is a range that will not bring about obstacle to the fundus imaging.

The plane reflection mirror 150 is disposed in a direction so that a direction of its normal C bisects an angle formed between a line segment A connecting the first focus 122 and the second focus 124 and a line segment B connecting the third focus 142 and the fourth focus 144. Thereby, the plane reflection mirror 150 reflects the light beam 102 reflected off the first reflection mirror 120 toward the second reflection mirror 140. Note that if the line segment A and the line segment B are in parallel, a direction which is orthogonal to those line segments may be handled as a normal C.

Note that the size of the plane reflection mirror 150 can be made the smallest by coinciding the position of the plane reflection mirror 150 with the second focus 124 (the third focus 142), as illustrated. The position of the plane reflection mirror 150, however, can also be disposed away from the second focus 124 (the third focus 142) as long as the above-described direction is maintained. That is, in the configuration, for example, shown in FIG. 2, as long as the scanning light beam led from the first reflection mirror to the second reflection mirror is not shielded partially, the plane reflection mirror 150 can be parallelly moved to an arbitrary position. In this case, it goes without saying that the focus of the one reflection mirror is made to coincide with the imaginary focus of the other reflection mirror formed by the reflection of the plane reflection mirror 150.

The first reflection mirror 120 and the second reflection mirror 140 are disposed in an arrangement relationship in which their reflection surfaces and rotation axes are in the same direction, that is, the rotation axes are disposed approximately on the −y side relative to the reflection surface. In other words, due to the presence of the plane reflection mirror 150, the first reflection mirror 120 and the second reflection mirror 140 do not face each other. Note that in FIG. 2 and in the other figures also, the first reflection mirror 120, the second reflection mirror 140, etc. are shown in a cross-section taken along the zy plane including the major axis.

The rotary ellipsoid of the first reflection mirror 120 and the rotary ellipsoid of the second reflection mirror 140 have an equal eccentricity to each other. Because the equal eccentricity to each other, the consistency of angular scanning of the light beam is maintained, and distortion does not occur in the fundus image obtained by light beam scanning. This will be described later. Also, as long as the size of the first reflection mirror 120 and the size of the second reflection mirror 140 are large enough to an extent that the light in the scanning range set at the two-dimensional scanning unit 130 can be reflected, the size of the first reflection mirror 120 and the size of the second reflection mirror 140 may be equal to each other, or may be different from each other. In the example in FIG. 2, the first reflection mirror 120 which is closer to the light source 110 is smaller than the second reflection mirror 140 which is closer to the eye 10. Thereby, the entire device can be reduced in size.

Figure 3:
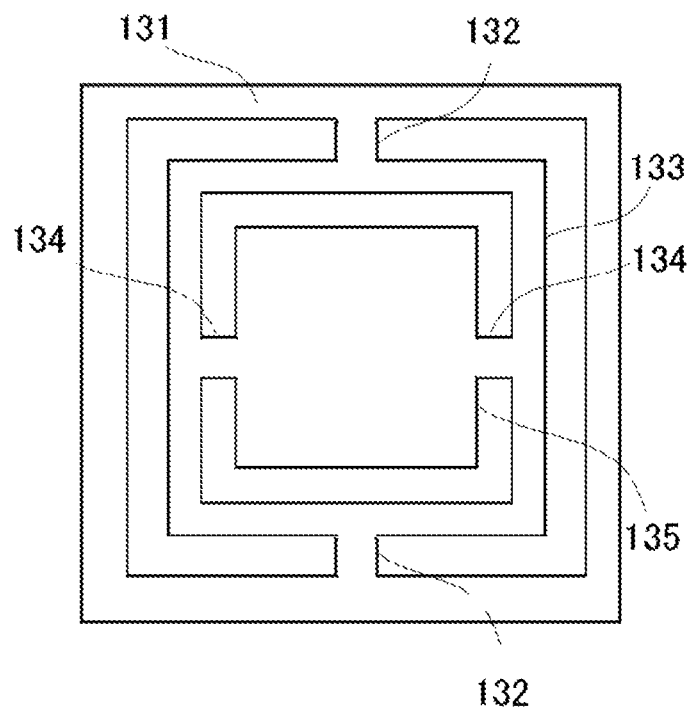
FIG. 3 is a schematic diagram of one example of a two-dimensional scanning unit 130.
Figure 3:
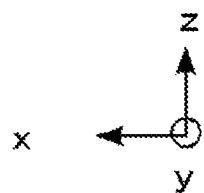

FIG. 3 is a schematic diagram of one example of the two-dimensional scanning unit 130. The two-dimensional scanning unit 130 has a body 131, a frame 133 which is supported by the junction 132 so as to be rotatable around the z axis relative to the body 131, and a reflection mirror 135 which is supported by the junction 134 so as to be rotatable around the x axis relative to the frame 133, and reflects a light beam. The two-dimensional scanning unit 130 has a so-called gimbal structure, and is configured with, for example, MEMS, and is, for example, electrostatically driven by the controlling unit 154.

In the above-described configuration, a pupil 12 of the subject is positioned within a predefined range (a range that allows the beam light to enter when the eye is placed in the vicinity of the fourth focus) so as to coincide with the fourth focus 144 of the second reflection mirror 140. The controlling unit 154 causes the light beam 102 to be emitted from the light source 110, and additionally by controlling a rotation amount of the two-dimensional scanning unit 130 to rotate the reflection mirror 135 around the z axis and around the x axis, the controlling unit 154 scans with the light beam 102 from the light source 110 in the z direction and the x direction.

The light beam 102 from the two-dimensional scanning unit 130 is reflected off the first reflection mirror 120, the plane reflection mirror 150, and the second reflection mirror 140 in this order, passes through the pupil 12, and reaches the retina. The light beam 102 reflected off the retina reversely traces the above-described optical path and reaches the half-silvered mirror 158. The light beam 102 that has been reflected off the half-silvered mirror 158 is detected at the detector 152. Based on the rotation amount of the two-dimensional scanning unit 130 controlled by the controlling unit 154, and the light amount detected by the detector 152, the image processing unit 156 two-dimensionally reconfigures an image of the retina, and outputs it to a monitor, etc.

Here, the relationship between the angular change of the light beam that the two-dimensional scanning unit 130 causes to be emitted from the first focus 122, and the angular change of the light beam which is reflected off the first reflection mirror 120 to be incident on the second focus 124 is considered. For example, the case where the two-dimensional scanning unit 130 performs scanning with the light beam by the angular change $\theta_{11}$ around the x axis from a certain angle, and the case where the two-dimensional scanning unit 130 scans with the light beam by the same angular change $\theta_{12}$ (that is, $\theta_{11}=\theta_{12}$) further around the x axis, as shown in FIG. 1, are considered.

Because in the above-described scanning, changes in curvatures of reflection portions of the first reflection mirror 120 differ respectively, respective angular changes $\theta_{21}$, $\theta_{22}$ at which the reflected light beam heads to the second focus 124 relative to the same angular changes $\theta_{11}$, $\theta_{12}$ differ in general (that is, $\theta_{21} \neq \theta_{22}$). Although the angles can be geometrically calculated respectively, such as $\theta_{21} < \theta_{22}$ in the example in FIG. 1.

In other words, the ratio between the angular change of the light beam which is emitted from the first focus 122, and the angular change of the light beam which is reflected off the first reflection mirror 120 and is incident on the second focus 124, corresponding to the angular change is not consistent ($\theta_{11}/\theta_{12} \neq \theta_{21}/\theta_{22}$).

An angle of incidence and an angle of reflection with respect to the plane mirror are equal. Thus, assuming that angular changes of reflection at the plane reflection mirror 150 relative to the angular changes $\theta_{21}$, $\theta_{22}$ are respectively $\theta_{31}$, $\theta_{32}$, $\theta_{21}=\theta_{31}$, $\theta_{22}=\theta_{32}$ are satisfied.

In the embodiment, the rotary ellipsoid of the first reflection mirror 120 and the rotary ellipsoid of the second reflection mirror 140 have equal eccentricity to each other, and additionally, the plane reflection mirror 150 is disposed in a direction so that a direction of its normal C bisects an angle formed between a line segment A and a line segment B. From the above, $\theta_{11}/\theta_{12}=\theta_{41}/\theta_{42}$ is satisfied. In other words, the ratio between the angular change of the light beam which is emitted from the first focus 122, and the angular change of the light beam which is incident on the fourth focus 144, corresponding to the angular changes is consistent. And, obviously, $\theta_{11}=\theta_{41}$, $\theta_{12}=\theta_{42}$ are satisfied.

In accordance with the above-described configuration, the two-dimensional image of the retina can be reconfigured without distortion in response to the rotation amount of the two-dimensional scanning unit 130. Also, because the two-dimensional scanning unit 130 is responsible for the two-dimensional scanning, and there is no mechanically movable portion during scanning at the common focus of the first reflection mirror 120 and the second reflection mirror 140, the entire device can be simplified and be reduced in size.

Figure 4:
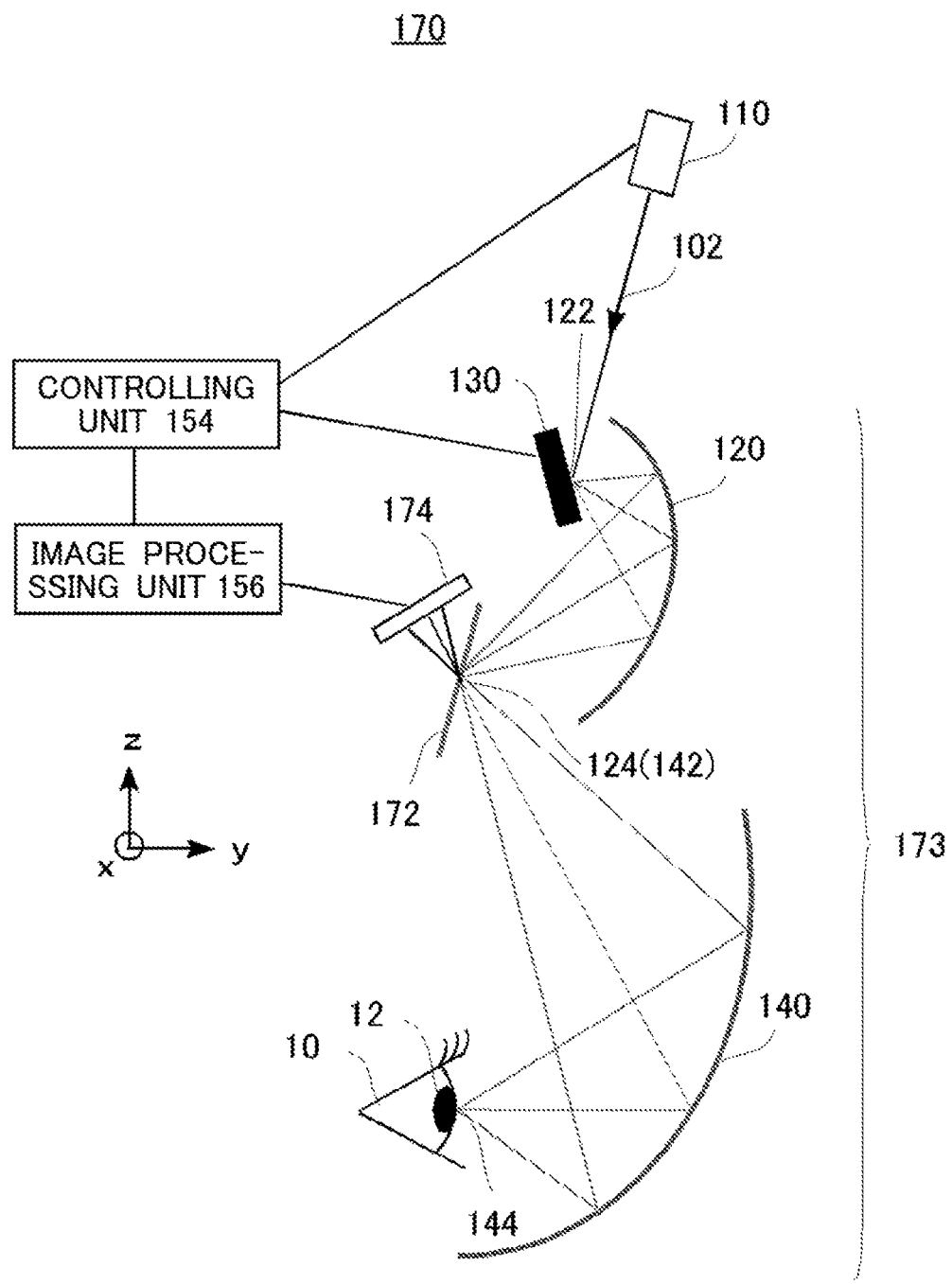
FIG. 4 is a schematic diagram of another fundus imaging system 170.

FIG. 4 is a schematic diagram of another fundus imaging system 170. In the fundus imaging system 170, the same configurations as the fundus imaging system 100 in FIG. 1 are given the same reference numbers, and a description about them will be omitted.

A scanning optical system 173 of the fundus imaging system 170 has a half-silvered mirror 172, instead of the plane reflection mirror 150 in FIG. 1, at the same position and in the same direction. The half-silvered mirror 172 reflects the light beam 102 from the first reflection mirror and leads it to the second reflection mirror 140, while the half-silvered mirror 172 transmits a part of the light beam 102, the part reflected off the fundus oculi which returns via the second reflection mirror 140.

Furthermore, instead of the detector 152 of the fundus imaging system 100, in the fundus imaging system 170, an light intensity sensor 174 is disposed on the opposite side to the second reflection mirror 140 in the half-silvered mirror 172. The light intensity sensor 174 (for example, a photodiode) detects an intensity of the light beam 102 which has passed through the half-silvered mirror 172.

By the above-described configuration, corresponding to the two-dimensionally scanning of the light beam 102 by the two-dimensional scanning unit 130, the image of the retina can be generated based on the light intensity detected by the light intensity sensor 174. Note that in a similar way to the previously described plane reflection mirror 150 shown in FIG. 1 and the FIG. 2, the position of the half-silvered mirror 172 can be disposed out of an focus position, as long as its arrangement direction is disposed in a direction so that the direction bisects an angle formed between a line segment A connecting the first focus 122 and the second focus 124 and a line segment B connecting the third focus 142 and the fourth focus 144.

Figure 5:
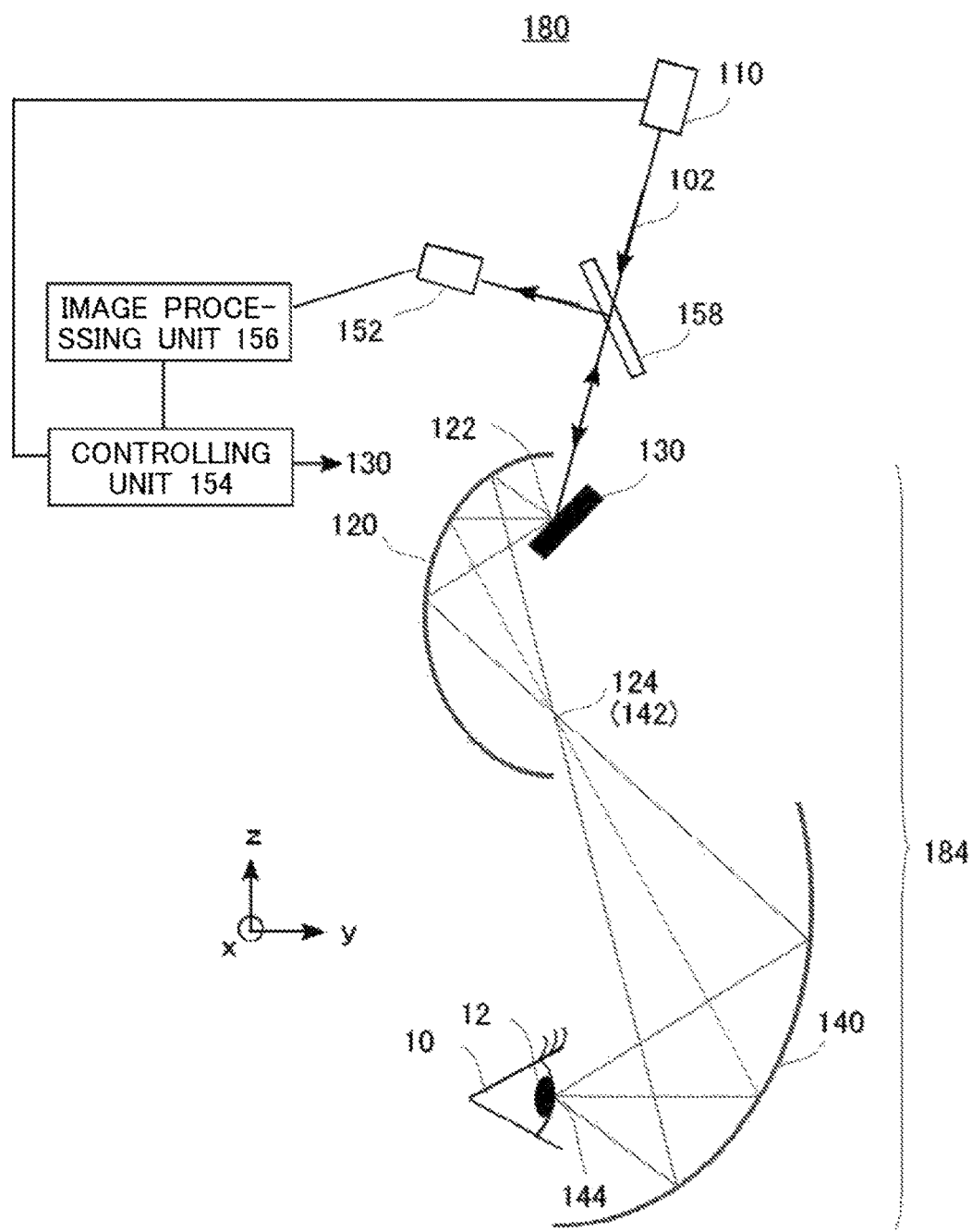
FIG. 5 is a schematic diagram of still another fundus imaging system 180.

FIG. 5 is a schematic diagram of still another fundus imaging system 180. In the fundus imaging system 180, the same configurations as the fundus imaging system 100 in FIG. 1 are given the same reference numbers, and a description about them will be omitted.

In a scanning optical system 184 of the fundus imaging system 180, the first reflection mirror 120 and the second reflection mirror 140 are disposed so as to face each other. The second focus 124 of the first reflection mirror 120 and the third focus 142 of the second reflection mirror 140 are disposed on the same straight line. In other words, a rotation axis of the elliptical mirror as the first reflection mirror 120 and a rotation axis of the elliptical mirror as the second reflection mirror 140 coincide with each other. In this configuration, different from the fundus imaging system 100, no optical member is disposed in the optical path to the first reflection mirror 120 and the second reflection mirror 140.

By the above-described configuration, the two-dimensional image of the retina can be reconfigured without distortion using fewer optical members.

All of the above-described embodiments use the shape which has reflection surfaces formed by the part of the rotary ellipsoid as the first reflection mirror 120 and the second reflection mirror 140. One or both of these may be replaced with other shapes. For example, a combination of a part of a first paraboloid rotary body with the first focus 122 focused and a part of a second paraboloid rotary body with the second focus 124 focused may be a first reflection mirror 120. In a similar way, a second reflection mirror 140 may be a combination of parts of two paraboloid rotary bodies.

Note that in the configuration of the above-described implementation, elliptical mirrors with equal eccentricity respectively are used as the first reflection mirror 120 and the second reflection mirror 140, it is possible to configure the system by combining two parabolic mirrors and a two-dimensional scanning mirror. A two-dimensional scanning mirror of a light beam is disposed on a focus of a first parabolic mirror, and the pupil 12 of the subject is positioned at a focus position of a next parabolic mirror. Although in a similar way as one elliptical mirror, inconsistency occurs in the angular scanning of the light beam with the reflection of one parabolic mirror, inconsistency in the angular scanning of the light beam can be cancelled by combining two same parabolic mirrors. By this configuration, a clear image with little distortion aberration at the fundus image can also be obtained.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

EXPLANATION OF REFERENCES

10: eye, 12: pupil, 100: fundus imaging system, 102: light beam, 110: light source, 112: scanning optical system, 120: first reflection mirror, 122: first focus, 124: second focus, 130: two-dimensional scanning unit, 131: body, 132: junction, 133: frame, 134: junction, 135: reflection mirror, 140: second reflection mirror, 142: third focus, 144: fourth focus, 150: plane reflection mirror, 152: detector, 154: controlling unit, 156: image processing unit, 158: half-silvered mirror, 170: fundus imaging system, 172: half-silvered mirror, 173: scanning optical system, 174: light intensity sensor, 180: fundus imaging system, and 184: scanning optical system

What is claimed is:

1. A fundus imaging system, comprising:
   a light source configured to emit a light beam;
   a first reflection mirror arranged to reflect the light beam incident on the first reflection mirror after passing through a first focus of the first reflection mirror so as to cause the light beam to pass through a second focus;
   a two-dimensional scanning unit disposed at a position of the first focus of the first reflection mirror and arranged to reflect a light beam incident on the two-dimensional scanning unit so as to scan a retina of a subject with the light beam in two-dimensional directions;
   a second reflection mirror arranged to reflect the light beam incident on the second reflection mirror after passing through a third focus so as to cause the light beam to pass through a fourth focus, the second reflection mirror being disposed so that a position of the third focus coincides with a position of the second focus of the first reflection mirror, a pupil of the subject being disposed at the fourth focus of the second reflection mirror;
   a plane reflection mirror arranged t reflect the light beam reflected off the first reflection mirror toward the second reflection mirror, the plane reflection mirror being arranged transmit a part of a light beam returned from the second reflection mirror; and
   a detecting unit arranged to detect the light beam that has been transmitted through the plane reflection mirror.

2. The fundus imaging system according to claim 1, wherein
   the two-dimensional scanning unit has:
     a body;
     a frame supported by the body so as to be rotatable in a first direction relative to the body; and
     a reflection mirror supported by the frame so as to be rotatable in a second direction orthogonal to the first direction relative to the body, the reflection mirror reflecting a light beam.

3. The fundus imaging system according to claim 1, wherein
   the plane reflection mirror having a normal in a direction that bisects an angle formed between a line segment connecting the first focus and the second focus and a line segment connecting the third focus and the fourth focus.

4. The fundus imaging system according to claim 1, wherein
   the first reflection mirror and the second reflection mirror have reflection surfaces formed by parts of rotary ellipsoids.

5. The fundus imaging system according to claim 4, wherein
   the rotary ellipsoids have an equal eccentricity to each other.

6. The fundus imaging system according to claim 5, wherein
   the first reflection mirror is smaller than the second reflection mirror.

7. The fundus imaging system according to claim 1, further comprising:
   an image processor configured to generate an image based on a light amount detected by the detecting unit.

8. The fundus imaging system according to claim 1, wherein
   the plane reflection mirror is moveable before scanning the light beam.

9. The fundus imaging system according to claim 1, wherein
   the light source is configured to emit an infrared beam.

10. The fundus imaging system according to claim 1, wherein
    the light source is configured to emit a visible light beam.

11. A scanning optical system comprising:
    a light source configured to emit light;
    a scanner configured to scan the light;
    a first mirror having a first focus and a second focus, the first mirror being configured to reflect the light passing through the first focus to the second focus, the first focus being a position at which the scanner is disposed;
    a second mirror having a third focus and a fourth focus, the second mirror being configured to reflect the light passing through the third focus to the fourth focus, the third focus being a position at which the second focus of the first mirror coincides, the fourth focus being a position at which a subject eye is disposed; and
    a half-mirror disposed in an optical path between the first mirror and the second mirror to reflect the light passing through the first mirror to the second mirror.

12. The scanning optical system according to claim 11, wherein
    the half-mirror has a normal that bisects an angle formed between a line segment of the first focus and second foci of the first mirror and a line segment of the third focus and fourth foci of the second mirror.

13. The scanning optical system according to claim 11, wherein
    the first mirror and the second mirror each has a reflection surface formed by a part of a rotary ellipsoid.

14. The scanning optical system according to claim 13, wherein
    the rotary ellipsoid has an equal eccentricity.

15. The scanning optical system according to claim 1, wherein
    the first mirror is smaller than the second mirror.

16. The scanning optical system according to claim 11, wherein
    the scanner is a two-dimensional scanner.

17. The scanning optical system according to claim 11, wherein
    the half-mirror is moveable before scanning the light.

18. The scanning optical system according to claim 11, wherein
    the half-mirror transmits infrared.

19. The scanning optical system according to claim 11, wherein
    the half-mirror transmits visible light.

20. The scanning optical system according to claim 11, wherein
the light source includes a plurality of light sources, and
the scanning optical system further comprises a beam combiner configured to place the plurality of light beams emitted by the plurality of light sources on the same optical path.

* * * * *